United States Patent [19]

Burk et al.

[11] 4,232,041
[45] Nov. 4, 1980

[54] AQUEOUS ANTIMICROBIAL COMPOSITION HAVING IMPROVED STABILITY

[75] Inventors: George A. Burk, Bay City; Charles E. Reineke, Midland, both of Mich.; Charles A. Wilson, Pittsburg, Calif.

[73] Assignee: The Dow Chemical Company, Midland, Mich.

[21] Appl. No.: 50,399

[22] Filed: Jun. 20, 1979

Related U.S. Application Data

[63] Continuation-in-part of Ser. No. 860,643, Dec. 14, 1977, abandoned.

[51] Int. Cl.$^3$ .................... A01N 37/18; A01N 37/43; A01N 34/40
[52] U.S. Cl. ................................... 424/304; 424/267; 424/320
[58] Field of Search ...................... 424/304, 267, 320

[56] References Cited

U.S. PATENT DOCUMENTS

| | | | |
|---|---|---|---|
| 3,689,660 | 9/1972 | Burk et al. | 424/304 |
| 3,751,444 | 8/1973 | Solem et al. | 260/465.4 |
| 4,022,605 | 5/1977 | Konya et al. | 424/304 |

*Primary Examiner*—Allen J. Robinson
*Attorney, Agent, or Firm*—James B. Guffey

[57] ABSTRACT

Aqueous antimicrobial compositions which comprise a halogenated amide antimicrobial, such as 2,2-dibromonitrilopropionamide, a water miscible organic solvent such as a straight chain polyalkylene glycol (e.g., polyethylene glycol 200) or an ether thereof (e.g., a mono- or di-lower alkyl and/or phenyl ether) and water and which have improved stability are obtained by ensuring that such compositions are substantially free of glycols having a molecular weight of less than about 70 and of salts of organic acids. The resulting improved compositions exhibit reduced rates of decomposition of the halogenated amide antimicrobial relative to the corresponding aqueous compositions containing salts of organic acids and/or glycols having a molecular weight of less than about 70.

15 Claims, No Drawings

AQUEOUS ANTIMICROBIAL COMPOSITION HAVING IMPROVED STABILITY

CROSS-REFERENCE TO RELATED APPLICATION

This application is a continuation-in-part of application Ser. No. 860,643, filed Dec. 14, 1977 and now abandoned.

BACKGROUND OF THE INVENTION

This invention relates to aqueous halogenated amide antimicrobial compositions having improved stability and to processes for their preparation.

Halogenated amides such as 2,2-dibromonitrilopropionamide are useful as antimicrobials in various applicaions. See, for example, Nolan et al., U.S. Pat. No. 2,419,888; Schmidt et al., U.S. Pat. No. 3,493,658; and CIBA S.A. Belgian Pat. No. 668,336. Certain halogenated amides are useful in the finishing of textiles, as taught by Chance et al., U.S. Pat. Nos. 3,350,164 and 3,403,174. Others are useful as slimicides in aqueous systems such as paper pulp and cooling towers and as sterilizing agents for dry cleaning fluids. See, for example, Wolf, U.S. Pat. No. 3,647,610; Wolf, U.S. Pat. 3,649,166; Wolf et al., "2,2-Dibromo-3-Nitrilopropionamide, A Compound with Slimicidal Activity", *Applied Microbiology*, Vol. 24, No. 4, pp. 581–584 (1972); and Moyle et al., U.S. Pat. No. 3,928,575.

In the storage, shipment and use of the aforementioned halogenated amide antimicrobial agents, it has heretofore been suggested to employ such antimicrobial agent in the form of a liquid concentrate composition wherein the halogenated amide is dissolved either in a straight chain polyalkylene glycol or in a mixture of such glycol with up to about 20 weight percent water on a total weight basis. Unfortunately, however, the presence of water in such compositions has been found to accelerate the decomposition of the halogenated amide therein and, indeed, at water contents above 20 weight percent the stability of the halogenated amide in the resulting aqueous compositions has been reported to be entirely unsatisfactory. See U.S. Pat. No. 3,689,660 and "Rates and Products of Decomposition of 2,2-Dibromo-3-Nitrilopropionamide," Exner et al., *J. Arg. Food Chem.*, Vol. 21, No. 5, pp. 838–842 (1973). Thus, in order to obtain adequate stability for most purposes, it has heretofore been generally necessary to either resort to essentially anhydrous liquid concentrate compositions or to at least limit the water content of such compositions to less than about 20 weight percent on a total weight basis. Similarly, it has also heretofore generally been necessary either to essentially exclude water from the ingredients used in the preparation of such compositions or at least to substantially limit the water content of such ingredients.

In view of the foregoing, it is highly desirable to provide a means of reducing the adverse impact of water upon the aforementioned liquid compositions and to thereby provide (a) aqueous halogenated amide antimicrobial compositions having improved stability and (b) an economical process for the preparation of suitably stable aqueous halogenated amide antimicrobial compositions. Moreover, it is especially desirable to provide such aqueous halogenated amide antimicrobial compositions (and preparation processes therefor) which have acceptable stability of the halogenated amide antimicrobial therein even at water contents in excess of 20 weight percent based on the total weight of such aqueous antimicrobial composition.

SUMMARY OF THE INVENTION

It has now been found that the major cause of the aforementioned problem of accelerated halogenated amide antimicrobial decomposition during storage under aqueous conditions has been the presence of certain impurities in the water miscible organic solvent heretofore employed in the preparation of the prior art antimicrobial compositions. Specifically, the problem of halogenated amide decomposition in the presence of water has been found to be substantially more pronounced when the water miscible organic solvent contains glycols having a molecular weight of less than about 70 and/or salts of organic acids, both of which are common impurities in many commercially available polyalkylene glycols which have heretofore been generally employed in the aforementioned liquid concentrate compositions. Thus, in one aspect, the instant invention is an aqueous antimicrobial composition having improved stability. Such composition typically has a pH of from about 2 to about 5 (preferably from about 3 to about 4), is substantially free of glycols having a molecular weight of less than about 70 and of salts of organic acids and comprises:

(1) a water miscible organic solvent;
(2) water; and
(3) a halogenated amide antimicrobial.

A particularly beneficial feature of the instant invention is that the substantial exclusion or elimination of the aforementioned impurities (i.e., the glycols having a molecular weight of less than about 70 and/or salts of organic acids) from the aqueous antimicrobial compositions hereof generally provides suitably stable aqueous halogenated amide antimicrobial compositions even at water contents in excess of 20 weight percent based upon the total weight of such composition. Accordingly, in one especially beneficial aspect, the instant invention is an aqueous antimicrobial composition which (a) is substantially free of glycols having a molecular weight of less than about 70 and of salts of organic acids; (b) has a pH of from about 2 to about 5 and (c) comprises:

(1) a halogenated amide antimicrobial compound;
(2) a water miscible organic solvent in an amount sufficient to dissolve said halogenated amide compound, said solvent being selected from the group consisting of polyalkylene and ethers thereof; and
(3) water in an amount greater than 20 weight percent based upon the total weight of such aqueous antimicrobial composition.

In another aspect, the instant invention is an improved process for preparing a halogenated amide antimicrobial composition which permits the use in such composition of the aqueous reaction medium in which the halogenated amide antimicrobial was prepared. Such process comprises preparing the halogenated amide antimicrobial by the acid catalyzed reaction of a non-halogenated amide with halogen in aqueous solution and dissolving the resulting aqueous reaction mixture in a water miscible organic solvent and such process is conducted under conditions substantially free of glycols having a molecular weight of less than about 70 and of salts of organic acids. Typically, such process also involves a step in which the pH of the reaction mixture (following the reaction and before dissolution in the organic solvent) is adjusted to a value of from about 5 to about 7 (preferably from about 5.5 to about 6.5) so that the composition resulting after dissolution in the organic solvent has a pH of from about 2 to about 5 (preferably from about 3 to about 4).

As used herein, the term "water miscible" means that the organic solvent is soluble in water (i.e., mixes or blends uniformly with water) at least to the degree required to achieve the desired solvent to water ratio in the aqueous composition and preferably the organic solvent is soluble in water in all proportions.

The terms "antimicrobial compound" and "halogenated amide antimicrobial" are used interchangeably herein and refer to halogenated amides which function as biocides (i.e., compounds which inhibit the growth of, or kill, microorganisms such as bacteria, molds, slimes, fungi, etc.).

The phrase "substantially free of glycols having a molecular weight of less than about 70 and of salts of organic acids" means that the composition contains less than about 1.0 (preferably less than about 0.5) weight percent of such glycols and less than about 0.1 (preferably less than about 0.05) weight percent of such salts, both percentages being on a total weight basis.

The aqueous antimicrobial compositions of the invention are useful as slimicides in aqueous systems such as paper pulping processes and cooling towers and as sterilizing agents for dry cleaning fluids. Such compositions exhibit improved stability toward decomposition of the halogenated amide antimicrobial for extended periods under a wide variety of storage, packaging and handling conditions. They are easily handled and can be employed in the above applications pursuant to conventional techniques such as those described in U.S. Pat. No. 3,689,660.

The indicated process for preparing the aqueous antimicrobial composition is advantageous in that suitably stable compositions can be prepared without separation of the halogenated amide antimicrobial from the aqueous medium in which it was prepared.

DETAILED DESCRIPTION OF THE INVENTION

Halogenated amide antimicrobials employed in the practice of this invention are alpha-haloamides; that is, compounds which contain an amide functionality (i.e., a moiety of the formula —C(O)—N<) and which have at least one halogen atom on a carbon atom located adjacent to (i.e., in the alpha position relative to) the carbonyl group (i.e., the —C(O)—group) of such amide functionality. Advantageously, such halogenated amide antimicrobials are halogenated nitrilopropionamides or halogenated malonic diamides having the formula:

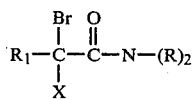

wherein:

X is hydrogen, halogen or a cyano radical, i.e., —C≡N (preferably hydrogen, chlorine or bromine);

each R group is independently hydrogen, a monovalent "saturated hydrocarbon radical" or an inertly substituted monovalent "saturated hydrocarbon radical" or the two R groups are, jointly, a divalent "saturated hydrocarbon radical", or an inertly substituted divalent "saturated hydrocarbon radical", which, taken with the adjacent nigrogen atom, forms a heterocyclic ring having from 4 to about 10 ring members; and $R_1$ is a cyano radical (i.e., —C≡N) or an amido radical having the formula:

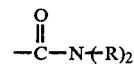

wherein R is as hereinbefore defined. (Preferably, $R_1$ is a cyano radical).

As used herein, the term "saturated hydrocarbon radical" refers to a hydrocarbon radical which is free from aliphatic carbon to carbon unsaturation. Thus, such term includes radicals such as alkyl, cycloalkyl, aryl, alkylaryl, arylalkyl, cycloalkylaryl, etc., and excludes radicals such as alkenyl, cycloalkenyl, alkynyl and the like.

As used herein, the term "inertly substituted saturated hydrocarbon radical" refers to a "saturated hydrocarbon radical" having one or more chain linkage or substituent which is "inert" in the sense that such chain linkage or substituent does not readily react with the ingredients of the aqueous antimicrobial composition. Suitable inertly substituted saturated hydrocarbon radicals thus include, for example, haloalkyl, haloaryl, halocycloalkyl, aminoalkyl, aminoaryl, aminocycloalkyl, hydroxyalkyl, hydroxyaryl, hydroxycycloalkyl, cyanoalkyl, cyanoaryl, cyanocycloalkyl and the like.

The aforementioned halogenated amide antimicrobials of the formula I thus include brominated nitrilopropionamides (i.e., compounds of the formula I wherein $R_1$ is a cyano radical), such as 2-bromo-3-nitrilopropionamide, 2-bromo-2,3-dinitrilopropionamide, 2,2-dibromo-3-nitrilopropionamide, N-(n-butyl)-2-bromo-3-nitrilopropionamide; N,N-dimethyl-2,2-dibromo-3-nitrilopropionamide, 2-chloro-2-bromo-3-nitrilopropionamide, N-(n-propyl)-2-iodo-2-bromo-3-nitrilopropionamide, N-methyl-N-ethyl-2-fluoro-2-bromo-3-nitrilopropionamide, N-phenyl-2-cyano-2-bromo-3-nitrilopropionamide, N-cyclohexyl-2,2-dibromo-3-nitrilopropionamide, N-benzyl-2-bromo-3-nitrilopropionamide, N-(2,2-dibromo-3-nitrilopropionoyl)piperidine and the like.

The aforementioned halogenated amide antimicrobials of the formula I also include mono- and di-bromomalonic diamides (i.e., compounds of the formula I wherein $R_1$ is an amido radical as hereinbefore described), such as 2-bromomalonic diamide, 2,2-dibromomalonic diamide, N-methyl-N'-ethyl-2-chloro-2-bromomalonic diamide, N-phenyl-2-iodo-2-bromomalonic diamide and the like.

Among the aforementioned halogenated amide antimicrobials, those wherein, in the formula I, $R_1$ is a cyano radical, X is hydrogen, chlorine or bromine and each R is independently hydrogen, lower alkyl (e.g., an alkyl group of from 1 to about 6 carbon atoms) or phenyl are preferred (especially those of the formula I wherein each R independently is hydrogen or methyl and X is hydrogen or bromine). Such preferred halogenated amide antimicrobials include 2-bromo-3-nitrilopropionamide, 2,2-dibromo-3-nitrilopropionamide, N-methyl-2-bromo-3-nitrilopropionamide, N-phenyl-2-bromo-2-chloro-3-nitrilopropionamide, N-methyl-2,2-dibromo-3-nitrilopropionamide, N,N-dimethyl-2-bromo-3-nitrilopropionamide, N,N-diethyl-2,2-dibromo-3-nitrilopropionamide, and N,N-dimethyl-2,2-dibromo-3-nitrilopropionamide.

Also of particular interest are the dibrominated nitrilopropionamides (i.e., the halogenated amide antimicrobials of the formula I wherein X is bromine and $R_1$ is cyano) wherein each R independently is hydrogen, lower alkyl or phenyl. Such compounds include 2,2-dibromo-3-nitrilopropionamide, N-(n-butyl)-2,2-dibromo-3-nitrilopropionamide, N,N-dimethyl-2,2-dibromo-3-nitrilopropionamide, N-phenyl-N-methyl-2,2-dibromo-3-nitrilopropionamide and the like; especially 2,2-dibromo-3-nitrilopropionamide.

The aqueous antimicrobial compositions of the invention normally contain from about 1 to about 25 percent, and more typically, from about 5 to about 20 percent, by weight of the hereinbefore described halogenated amide antimicrobial based upon the total weight of the composition. However, the prior art problem of decomposition of the halogenated amide antimicrobials in the presence of the aforementioned impurities (i.e., glycols having a molecular weight of less than about 70 and/or salts of organic acids) has been observed to be more pronounced when the aqueous compositions contain less than about 20 percent by weight of the antimicrobial on a total weight basis. Thus, aqueous antimicrobial compositions which, by virtue of the relatively more pronounced benefits obtained by exclusion of such impurities, are of particular interest comprise from about 1 to about 15, preferably from about 1 to about 10, most preferably from about 1 to about 5, weight percent of the total composition.

In the composition of this invention, the aforementioned halogenated amide antimicrobial is dissolved in a mixture of water and a water miscible organic solvent. Suitable organic solvents include any water miscible organic solvent in which the halogenated amide antimicrobial is at least partially soluble. Preferably, the organic solvent is one in which the halogenated amide antimicrobial is soluble at normal room temperature (i.e., from about 20° to about 25° C.) to the extent of at least about 5 parts by weight of the antimicrobial in about 95 parts by weight of the solvent. The most preferred water miscible organic solvents are those in which the antimicrobial is soluble to the extent of at least about 10 (especially at least about 20) parts by weight of the antimicrobial in about 80 parts by weight of the solvent at normal room temperatures (i.e., from about 20° to about 25° C.)

Advantageously, the organic solvent is a polyalkylene glycol or an ether thereof, especially a normally liquid straight chain polyalkylene glycol or a mono- or di-lower saturated hydrocarbyl ether thereof wherein the term "saturated hydrocarbyl" refers to a monovalent saturated hydrocarbon radical as hereinbefore defined.

Generally, such polyalkylene glycols and polyalkylene glycol ethers have a weight average molecular weight (Mw) of from about 75 to about 1000. Such average molecular weights are hereinafter designated for the particular glycols involved by placing a numeral representing the weight average molecular weight after the glycol name.

Of particular interest in the practice of the invention are the polyalkylene glycols of the ethylene, trimethylene or tetramethylene series and the mono- and di-lower (e.g., containing from 1 to about 6 carbon atoms) saturated hydrocarbyl ethers thereof. Such particularly advantageous solvents thus include polyethylene glycols, trimethylene glycols, tetramethylene glycols and the mono- and di-lower saturated hydrocarbyl (e.g., lower alkyl and phenyl) ethers of such glycols. Examples of such glycols and ethers include 1,4-butanediol, triethylene glycol, polyethylene glycol 200, tetraethylene glycol, polyethylene glycol 400, diethylene glycol dimethyl ether, diethylene glycol phenyl ether, diethylene glycol ethyl phenyl ether, polytrimethylene glycol 200, diethylene glycol, triethylene glycol methyl ether and polyethylene glycol 600.

Preferably, the polyalkylene glycol or ether ingredient is a polyethylene glycol, or a mixture of polyethylene glycols, having Mw of from about 175 to about 250. Most preferably the polyalkylene glycol ingredient is polyethylene glycol 200.

As has been noted, this invention is based upon the discovery that the prior art problem of pronounced halogenated amide antimicrobial decomposition in aqueous liquid concentrate compositions is attributable to the presence of certain impurities which have been present in the water miscible organic solvents typically employed in the prior art aqueous halogenated amide antimicrobial compositions. Specifically, such impurities are glycols having a molecular weight of less than about 70 and/or salts of organic acids such an ammonium salts or alkali metal or alkaline earth metal (e.g., sodium, potassium or calcium), salts of organic acids (e.g., mono- and polycarboxylic acids) such as acetic acid, propionic acid, butyric acid, adipic acid, citric acid, etc. Consequently, since such impurities are commonly found in varying amounts in unpurified commercial grades of the aforementioned polyalkylene glycols and polyalkylene glycol ethers, care must be exercised in the practice of this invention either to employ grades of such glycols or ethers which have previously been purified to remove such impurities or to first purify (e.g., by distillation, etc.) the less pure commercial grades to remove such impurities prior to use in the instant invention. In short, it is a requirement in the practice of this invention that the aforementioned water miscible organic solvent be substantially free (e.g., contain less than about 1.0, preferably less than about 0.5, weight percent based upon the weight of solvent) of glycols having a molecular weight of less than about 70 and that such solvent also be substantially free (e.g., contain less than about 0.1, preferably less than about 0.05, weight percent based upon the weight of solvent) of salts of organic acids.

The amount of the aforementioned water miscible organic solvent employed in the practice of the invention is not particularly critical so long as a sufficient amount is employed to prevent precipitation of the halogenated amide antimicrobial during shipping, storage and use of the aqueous antimicrobial composition. The amount of the organic solvent employed will thus depend upon such factors as the solubility of the halogenated amide antimicrobial in the organic solvent, the desired concentration of the halogenated amide antimicrobial in the composition, and the like. However, as a general rule, the organic solvent constitutes from about 5 to about 90, preferably from about 10 to about 80, more preferably from about 25 to about 75, most preferably from about 35 to about 70, percent by weight of the total antimicrobial composition.

The amount of water contained by the aqueous antimicrobial composition of the invention is likewise not particularly critical to the practice of the invention and, as a general rule, the compositions of the invention employ water in an amount of from about 5 to about 90 weight percent based upon the total weight of the aqueous antimicrobial composition. However, as has been previously noted, the aforementioned prior art problem of accelerated halogenated amide antimicrobial decomposition under aqueous conditions is generally more pronounced in compositions having relatively large water contents and has been observed to be especially severe at water contents of greater than 20 weight percent based upon the total weight of the aqueous composition. Thus, the stability benefits obtained by the practice of this invention (i.e., by elimination of the aforementioned impurities) are relatively greater in compositions having relatively large water contents. Accordingly, compositions in which the practice of this invention is especially advantageous contain water in an amount of from about 10 to about 85 (preferably from about 15 to about 70, more preferably from greater than 20 up to about 60 and most preferably from about 25 to about 50) weight percent based upon the total weight of the aqueous antimicrobial composition and, indeed, a particularly beneficial aspect of the instant invention is that it permits obtention of aqueous compositions having suitable stability even at water contents in excess of 20 weight percent based upon the total weight of such aqueous antimicrobial composition.

In addition to the hereinbefore described ingredients, the aqueous antimicrobial compositions can optionally contain other ingredients. Such other ingredients can be inert in the sense that they neither inhibit nor accelerate decomposition of the halogenated amide. Alternatively, such other ingredients can be of a type which either accelerate or inhibit decomposition of the halogenated amide antimicrobial.

Thus, for example, the aqueous antimicrobial composition of the invention can optionally contain stabilizing ingredients such as those disclosed in several commonly owned applications which were all filed Dec. 14, 1977. Examples of such optional stabilizing ingredients thus include acids or anhydrides (e.g., acetic acid, ethylenediaminetetraacetic acid, succinic acid, succinic anhydride, glycolic acid, etc.) as disclosed by George A. Burk in Ser. No. 860,498; carbamoyl or sulfamoyl compounds (e.g., N-methyl urea, N,N-diethyl urea, biuret, sulfamide, oxamide, N,N-dimethylformamide, caprolactam, N-methyl-2-pyrrolidone, dimethylhydantoin, succinimide, etc.) as disclosed by George A. Burk and Charles E. Reineke in Ser. No. 860,541; cyclic ethers (e.g., 1,4-dioxane, tetrahydrofuran, sym-trioxane, N-methyl morpholine, etc.) as disclosed by George A. Burk and Charles A. Wilson in Ser. No. 860,497; aldehydes (e.g., formaldehyde, paraformaldehyde, vanillin, etc.) as disclosed by George A. Burk, Charles A. Wilson and Charles E. Reineke in Ser. No. 860,642; quaternary ammonium or phosphonium salts (e.g., methyl triphenyl phosphonium bromide, n-$C_{12}$-$C_{18}$ alkyl dimethyl benzyl ammonium chloride, etc.) as disclosed by George A. Burk in Ser. No. 860,543; and azine or nitrile compounds (e.g., cyanuric acid, 2-chloro-4,6-bis(ethylamino)-s-triazine, cyanoguanidine, succinonitrile, etc.) as disclosed by George A. Burk in Ser. No. 860,540. When such optional stabilizing ingredients are employed, they are generally used in an amount sufficient to measurably reduce the decomposition rate of the halogenated amide antimicrobial in the aqueous antimicrobial composition (i.e., in a stabilizing amount). Such reduction in the halogenated amide antimicrobial decomposition is, of course, relative to the decomposition rate encountered with a corresponding aqueous composition in the absence of stabilizer under the same test conditions and such reduction is deemed to be "measurable" if it is detectible (and reproducible) by the iodometric test method which is described hereinafter in conjunction with the working examples. Advantageously, such optional stabilizing ingredients, when used, are employed in an amount sufficient to reduce by at least about 20 (preferably at least about 30 and most preferably at least about 40) percent the amount of the halogenated amide antimicrobial which decomposes during about 15 days (preferably about 30 days) at 50° C. based upon the amount of decomposition which occurs under the same conditions in the absence of the stabilizing ingredient. While the amount of optional stabilizing ingredient required to accomplish the desired degree of stabilization in a given instance can vary, as a general rule, the optional stabilizing ingredient, if employed, will constitute between about 0.05 and about 10, preferably between about 0.1 and about 5, most preferably between about 0.5 and about 2, percent by weight of the total composition.

The aforementioned optional stabilizing ingredients are not generally required for suitable stability in the compositions of the invention since such compositions are free from the destabilizing effects of the hereinbefore described impurities. However, in those instance wherein the compositions of the invention comprise other destabilizing ingredients or impurities, it is preferable that such compositions also comprise one or more of the aforementioned optional stabilzing ingredients in addition to being substantially free from the aforementioned impurities. Thus, for example, when the composition of the invention is prepared pursuant to the hereinafter described process (in which the aqueous reaction medium of the halogenated amide preparation reaction forms part of the aqueous composition), the resulting aqueous halogenated amide composition will generally contain halide salts (e.g., alkali metal or alkaline earth metal halides such as sodium bromide, sodium chloride, potassium chloride, potassium bromide, calcium bromide, calcium chloride, etc.). Such halide salts are generated in the halogenated amide preparation process and have also been found to adversely affect the stability of the halogenated antimicrobial in the aqueous liquid concentrate compositions thereof. Accordingly, when the compositions of the invention contain such halide salts (from the aforementioned process or from some other source), it is beneficial (and therefore preferred) to also employ the aforementioned optional stabilizing ingredients in such compositions.

The order of combination of the hereinbefore described ingredients is not critical to the practice of the invention. However, when the aforementioned optional stabilizing ingredients are employed, it is generally desirable to avoid prolonged exposure of the antimicrobial compound to the water in the composition prior to addition of such stabilizing ingredient thereto. Similarly, it is generally desirable, in order to retain optimum antimicrobial activity, to prepare, store, transport and handle the compositions of the invention at the lowest practicable temperature (normally ambient temperature).

As has been noted, elimination of the hereinbefore described impurities (i.e., glycols having a molecular weight of less than about 70 and salts of organic acids) from aqueous halogenated amide antimicrobial compositions has been found to reduce the halogenated amide antimicrobial decomposition rate in a mixture of the aforementioned organic solvent and water. A particularly beneficial result of such phenomenon (especially when used in conjunction with the stabilizing phenomenon of the aforementioned optional stabilizing ingredients) is that suitably stable halogenated amide antimicrobial compositions can be prepared directly from a mixture of the antimicrobial and the aqueous reaction medium in which it was prepared. Specifically, separation of the halogenated amide antimicrobial from its aqueous reaction medium is conveniently eliminated by incorporating such reaction medium into the antimicrobial composition. The adverse impact of the resulting presence of water which would otherwise occur is prevented by ensuring that the resulting comosition is substantially free from the aforementioned impurities (for example, by employing ingredients such as solvents, etc. which are substantially free of such impurities) and preferably by also adding the aforementioned optional stabilizing ingredients.

Thus, in one aspect this invention is a process for preparing the aforementioned aqueous antimicrobial compositions, which process comprises (a) preparing the halogenated amide antimicrobial by the acid catalyzed reaction of the corresponding nonhalogenated amide with halogen in aqueous solution and dissolving the resulting aqueous reaction mixture in the hereinbefore described water miscible organic solvent; (b) by conducting such process under conditions which are substantially free of glycols having a molecular weight of less than about 70 and of salts of organic acids; and (c) optionally, but preferably, adding to the reaction mixture, or to the water-soluble organic solvent solution thereof, a stabilizing amount of one or more of the aforementioned optional stabilizing ingredients (especially paraformaldehyde, caprolactam, succinimide, or ethylenediaminetetraacetic acid). Typically, the aforementioned process also comprises an additional step in which the pH of the reaction mixture, the organic solvent solution, or the stabilized organic solvent solution is adjusted such that the resulting composition has a pH of from about 2 to about 5, preferably from about 3 to about 4. Preferably, such pH adjustment step is performed prior to dissolution of the reaction mixture in the organic solvent. In such preferred instance, adjustment of the reaction mixture pH to a value of from about 5 to about 7 (preferably from about 5.5 to about 6.5) typically results in the desired pH for the final composition resulting after dissolution of the reaction mixture in the aforementioned organic solvent.

The particular reagent employed to achieve the aforementioned pH adjustment in such step is not particularly critical. However, as a general rule, alkali metal or alkaline earth metal carbonates or bicarbonates (especially sodium carbonate) are advantageously employed.

The preparation of the halogenated amide antimicrobial (i.e., step (a) above) can be accomplished in any convenient conventional manner. Thus, for example, the halogenated amide antimicrobial can be prepared by the acid catalyzed reaction of the corresponding non-halogenated amide (e.g., cyanoacetamide, malonic diamide and N-substituted derivatives thereof) with halogen (especially bromine) in aqueous solution, preferably at a temperature of less than about 40° C. and preferably at a hydrogen halide (which is a reaction by-product) concentration of less than about 20 weight percent on a total weight basis.

Preferably, however, the initial step of such process is performed pursuant to the improved procedure which is disclosed by U.S. Pat. No. 3,751,444. In such preferred process for preparing the halogenated amide antimicrobial, the improved aspect comprises introducing a water-soluble bromate into the aqueous reaction medium. Further details relating to the practice of such preferred initial step are found in U.S. Pat. No. 3,751,444, the disclosure of which is hereby incorporated by reference.

After the halogenated amide antimicrobial has been prepared in the aforementioned manner, the resulting reaction mixture is dissolved in the hereinbefore described organic solvent. Such dissolution step is performed either before or after the optional but preferable addition of the aforementioned stabilizing ingredient and without isolation of the halogenated amide antimicrobial from the aqueous reaction medium.

In the aforementioned process, it is generally desirable to avoid prolonged exposure of the halogenated amide antimicrobial to the aqueous reaction medium in the absence of the stabilizing ingredient (if such ingredient is to be employed) in order to minimize decomposition of the halogenated amide product prior to stabilization. In addition, the pH adjustment step is also desirably accomplished without prolonged delay since the decomposition rate of the halogenated amide antimicrobial is generally pH dependent and since such decomposition rate is typically minimized within the indicated pH range. In addition, since the rate of decomposition of the halogenated amide anti-microbial increases with increased temperature, it is preferable to conduct the aforementioned individual process steps (and to store, transport and handle the resulting aqueous antimicrobial compositions) at ambient temperature (e.g., from about 20° to about 25° C.) or less in order to avoid excessive decomposition of the antimicrobial during such operations.

The practice of the instant invention is further illustrated by the following examples. In such examples, all weight percentages are on a total weight basis unless otherwise indicated.

EXAMPLE 1

Stable Aqueous Composition of 2,2-Dibromo-3-Nitrilopropionamide Employing Purified Tetraethylene Glycol as the Solvent These experiments illustrate the destabilizing effect of common impurities in a polyalkylene glycol solvent (which commonly arise in the manufacture of such solvents) upon 2,2-dibromo-3-nitrilopropionamide (DBNPA) dissolved in a mixture of such solvent and water. Also illustrated is the improved DBNPA stability in a glycol-water solution wherein the glycol has been purified to remove substantially all of such impurities.

Control 1

A 2.5 g portion of 2,2-dibromo-3-nitrilopropionamide (DBNPA) is placed in a 2 ounce amber bottle. To this is added a 23.75 g portion of water and a 23.75 g portion of a commercially available unpurified mixture of polyethylene glycols having a weight averaged molecular weight of about 200. Such polyethylene glycol mixture also contains an undetermined amount of residual unpolymerized ethylene glycol monomer (molecular weight=62) and an undetermined amount of sodium acetate resulting from neutralization of excess sodium hydroxide remaining following polymerization of the ethylene glycol monomer.

EXAMPLE 1

In a second 2 ounce amber bottle is placed a 2.5 g portion of DBNPA, a 23.75 g portion of water and a 23.75 g portion of purified tetraethylene glycol. The purified tetraethylene glycol is substantially free of ethylene glycol monomer and of salts resulting from sodium hydroxide neutralization in the polyethylene glycol manufacturing operation.

The contents of both of the bottles are mixed until all of the ingredients are dissolved. The dissolution is accompanied by a temperature rise of about 5° C. After the heat of dissolution has dissipated, the initial DBNPA content is verified by iodometry. The bottles are then closed with a polyethylene lined cap and placed in a constant temperature oven at 50° C. for accelerated decomposition testing. The samples are removed after 19 days and the extent of DBNPA decomposition is determined by iodometry. In such test method, an excess of potassium iodide (KI) is added to the antimicrobial composition and the amount of elemental iodine which has been liberated from the KI (via oxidation of the KI by the DBNPA) is determined by titration with a standard solution of sodium thiosulfate. The amount of DBNPA present in the composition tested is then calculated on the basis of the amount of elemental iodine liberated thereby. (It should be noted that since certain of the intermediate decomposition products of DBNPA are also oxidizing agents, the indicated test method does not, strictly speaking, provide an exact measure of DBNPA content. However, such test method does provide a measure of the amount of DBNPA which has completely decomposed to the ultimate non-oxidizing species and thus provides a relative measure of the stability of the DBNPA compositions tested.)

The results of the aforementioned iodometric testing indicates that after 19 days at 50° C. the aqueous antimicrobial composition of Example 1 (i.e., using the purified tetraethylene glycol solvent) contains 90 percent of its original DBNPA content. In contrast, the composition of Control 1 (i.e., using the unpurified polyethylene glycol 200 solvent) contains only 74 percent of its original DBNPA content after the same time period at 50° C. Elimination of the indicated impurities from the solvent of Control 1 (to thereby provide the composition of Example 1) is thus observed to reduce the DBNPA decomposition by about 62 percent based upon that which occurs in the presence of such impurities, i.e., $[(0.90-0.74) \div (1.00-0.74)] \times 100\% = 62\%$

EXAMPLES 2 AND 3

Aqueous Solution of DBNPA in Purified Tetraethylene Glycol Prepared Directly from the Aqueous DBNPA Reaction Medium A 26.0 g quantity (i.e., 0.3 mole) of commercial cyanoacetamide is dissolved in 95 ml of water and is then reacted with a 48 g portion (i.e., 0.3 mole) of bromine for half an hour at 22°–26° C. Thereafter, a 15.1 g portion of NaBrO$_3$ (in the form of a concentrated aqueous solution thereof) is slowly added to the reaction mixture over a 1½ hour period while continuing the reaction at 22°–26° C. An additional 2.0 g portion of bromine is then added and the reaction is continued for an additional 2 hour period.

The pH of the resulting reaction mixture is then adjusted to 6.0 with Na$_2$CO$_3$ and a 180 g portion of purified tetraethylene glycol (i.e., substantially free of glycols other than tetraethylene glycol and of salts of organic acids) is added to dissolve the reaction mixture. The resultant solution has a pH of 3.5 and contains 19.3 weight percent DBNPA as determined by iodometric titration; representing a 98 percent yield of DBNPA.

One portion of the resulting reaction mixture solution (i.e., the composition of Example 2) is stored at 50° C. and analyzed for retained DBNPA after various storage intervals by iodometric titration. A second portion of the resulting reaction mixture solution is stabilized with 1 weight percent paraformaldehyde (thereby forming the composition of Example 3) and is analyzed (by iodometric titration) for retained DBNPA content after various storage intervals at 50° C.

In a similar fashion, comparative compositions (i.e., Controls 2 and 3) are prepared which correspond to the compositions of Examples 2 and 3, respectively, except that an unpurified mixture of polyethylene glycols (having a weight averaged molecular weight of 200 and containing an undetermined quantity of residual ethylene glycol monomer and neutralization salts; probably sodium acetate) is employed as the solvent in place of the purified tetraethylene glycol of Examples 2 and 3. These compositions are also analyzed by iodometric titration for retained DBNPA content after various storage intervals at 50° C.

The retained DBNPA results for the compositions of Examples 2 and 3 and for the comparative compositions of Controls 2 and 3 are presented in Table I below.

TABLE I

DBNPA Retention After The Indicated Storage Intervals At 50° C.

| Composition Ingredients[1] | Example 2 | Control 2 | Example 3 | Control 3 |
|---|---|---|---|---|
| DBNPA | 19 | 19 | 19 | 19 |
| Purified Tetraethylene Glycol | 42 | — | 42 | — |
| Commercial Grade Polyethylene Glycol 200 | — | 42 | — | 42 |
| Water | 35 | 35 | 35 | 35 |
| Sodium Bromide[2] | 3 | 3 | 3 | 3 |
| Paraformaldehyde[3] | — | — | 1 | 1 |

| Percentage of Initial DBNPA Retained After the Indicated Storage Time @ 50° C. | Example 2 | Control 2 | Example 3 | Control 3 |
|---|---|---|---|---|
| 9 Days | — | 93% | — | 96% |
| 11 Days | 95% | — | 97% | — |
| 14 Days | — | — | — | — |
| 24 Days | — | 76% | — | 88% |
| 25 Days | 87% | — | — | — |
| 28 Days | 81% | — | 90% | — |

[1]Ingredients given in parts by weight.
[2]Generated during the preparation of the DBNPA and carried into the compositions in the aqueous DBNPA reaction medium.
[3]Stabilizer.

The results in Table I show that the compositions employing the purified tetraethylene glycol retain more DBNPA after the same (or longer) storage intervals than do the corresponding compositions employing unpurified polyethylene glycol 200 as the solvent in place of the tetraethylene glycol. (Compare Examples 2 and 3, respectively, with Controls 2 and 3.)

The benefits of employing paraformaldehyde as a stabilizer in conjunction with the use of the purified tetraethylene glycol solvent and the aqueous DBNPA reaction medium is observed by comparing the retained DBNPA results for the composition of Example 3 with those for the composition of Example 2. Specifically, such comparison illustrates that the use of such stabilizer in the embodiment employing the aqueous antimicrobial reaction medium provides further improvement in the antimicrobial stability.

While the practice of the invention has been illustrated with reference to particular embodiments and examples, it should be understood that such embodiments and examples are not intended to limit the scope of the instantly claimed invention.

What is claimed is:

1. An aqueous antimicrobial composition (a) which is substantially free of glycols having a molecular weight of less than about 70 and of salts of organic acids and which thereby has improved stability of the active antimicrobial ingredient therein; (b) which has a pH of from about 2 to about 5; and (c) which comprises, based upon the total weight of such composition:

(1) from about 1 to about 25 weight percent of an alpha-halogenated amide antimicrobial compound of the formula:

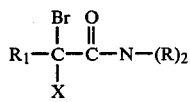

wherein:
   X is hydrogen, halogen or a cyano radical;
   each R group is independently hydrogen, a monovalent saturated hydrocarbon radical or an inertly substituted monovalent saturated hydrocarbon radical or the two R groups are jointly a divalent saturated hydrocarbon radical or an inertly substituted divalent saturated hydrocarbon radical which, taken with the adjacent nitrogen atom, forms a heterocyclic ring having from 4 to about 10 ring members; and
   $R_1$ is a cyano radical or an amido radical of the formula:

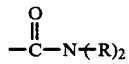

wherein R is as hereinbefore defined;

(2) a water miscible organic solvent in an amount sufficient to dissolve said alpha-halogenated amide, said solvent being selected from the group consisting of normally liquid polyalkylene glycols of the ethylene, trimethylene, or tetramethylene series and the mono- and di-saturated hydrocarbyl ethers thereof; and (3) water in an amount greater than 20 weight percent based upon the total weight of the aqueous antimicrobial composition.

2. The composition of claim 1 wherein the halogenated amide antimicrobial compound constitutes from about 5 to about 20 weight percent of the total composition.

3. The composition of claim 2 wherein the polyalkylene glycol or ether thereof is a normally liquid, a straight chain polyalkylene glycol of the ethylene, trimethylene or tetramethylene series or a mono- or di-lower alkyl or phenyl ether thereof.

4. The composition of claim 3 wherein the polyalkylene glycol or ether thereof has a weight average molecular weight of from about 75 to about 1000.

5. The composition of claim 1 wherein, in the halogenated amide antimicrobial compound:
   X is hydrogen, bromine or chlorine;
   each R group is independently hydrogen, a monovalent saturated hydrocarbon radical or an inertly substituted monovalent saturated hydrocarbon radical; and
   $R_1$ is a cyano radical.

6. The composition of claim 1 wherein, in the halogenated amide antimicrobial compound, X is hydrogen, chlorine or bromine and $R_1$ is a cyano radical.

7. The composition of claim 1 wherein the halogenated amide antimicrobial compound is 2,2-dibromo-3-nitrilopropionamide.

8. The composition of claim 1 wherein the water constitutes from about 25 to about 50 weight percent of the gaseous antimicrobial composition.

9. The composition of claim 1 wherein the water miscible organic solvent is tetraethylene glycol and the halogenated amide antimicrobial compound is 2,2-dibromo-3-nitrilopropionamide.

10. The composition of claim 1 wherein:
    (a) the halogenated amide antimicrobial compound constitutes from about 5 to about 20 weight percent of the total composition;
    (b) the water constitutes from greater than 20 up to about 60 weight percent of the total composition;
    (c) the water miscible organic solvent constitutes from about 25 to about 75 weight percent of the total composition; and
    (d) the composition contains less than about 1.0 weight percent, based upon the total weight of the composition, of glycols having a molecular weight of less than about 70 and less than about 0.1 weight percent, based upon the total weight of the composition, of salts of organic acids.

11. A process for preparing the aqueous antimicrobial composition of claim 1 which process (1) is conducted under conditions which are substantially free of glycols having a molecular weight of less than about 70 and of salts of organic acids and (2) comprises the steps of:
    (a) preparing the alpha-halogenated amide antimicrobial by the acid catalyzed reaction of the corresponding nonhalogenated amide with halogen in aqueous solution at a temperature of less than about 40° C. and at a hydrogen halide concentration which is less than about 20 weight percent on a total weight basis but which is sufficient to catalyze the reaction;
    (b) dissolving the resulting aqueous reaction mixture in the water miscible organic solvent; and
    (c) adjusting the pH of the reaction mixture or the organic solvent solution thereof such that the aqueous antimicrobial composition has a pH of from about 2 to about 5.

12. The process of claim 11 in which the pH adjustment step comprises adjusting the pH of the aqueous reaction mixture to a value of from about 5 to about 7 prior to dissolution of such reaction mixture in the water miscible organic solvent.

13. The process of claim 11 which further comprises a step of adding to the reaction mixture, or to the solution thereof in the water miscible organic solvent, a stabilizing amount of one or more stabilizing ingredients selected from the group consisting of acids, anhydrides, carbamoyl compounds, sulfamoyl compounds, cyclic ethers, aldehydes, quaternary ammonium compounds, quaternary phosphonium compounds, azine compounds and nitrile compounds.

14. The process of claim 11 wherein a water-soluble bromate is introduced to the aqueous reaction medium during the acid catalyzed reaction to prepare the halogenated amide antimicrobial and the pH of the reaction or the organic solvent solution thereof is adjusted by the addition of an alkali metal, or an alkaline earth metal, carbonate or bicarbonate such that the aqueous antimicrobial composition has a value of from about 3 to about 4.

15. The process of claim 14 wherein:
(1) the halogenated amide antimicrobial is 2,2-dibromo-3-nitrilopropionamide and the halogen is bromine;
(2) the water miscible organic solvent is tetraethylene glycol; and
(3) the stabilizing ingredient is paraformaldehyde, caprolactam, succinimide or ethylenediaminetetraacetic acid.

* * * * *